United States Patent [19]

West et al.

[11] Patent Number: 5,651,876

[45] Date of Patent: Jul. 29, 1997

[54] INTERFERENCE SUPPRESSING BUFFER

[75] Inventors: Steven J. West, Hull, Mass.; John K. Tsagatakis, Iraklion, Greece; Xiaowen Wen, Lexington, Mass.

[73] Assignee: Orion Research Inc., Beverly, Mass.

[21] Appl. No.: 397,623

[22] Filed: Mar. 2, 1995

[51] Int. Cl.$^6$ .................................................. G01N 27/333
[52] U.S. Cl. ...................... 205/789.5; 204/403; 204/416; 205/781.5; 422/82.03; 436/8; 436/18; 436/79
[58] Field of Search ........................ 204/403, 416, 204/418, 419; 205/781.5, 789.5; 252/518, 521; 422/68.1, 69, 82.03; 436/8, 28, 74, 18, 79, 800

[56] References Cited

U.S. PATENT DOCUMENTS

| | | | |
|---|---|---|---|
| 3,754,864 | 8/1973 | Gindler | 436/74 |
| 4,645,744 | 2/1987 | Charlton et al. | 436/74 |
| 5,264,348 | 11/1993 | Schick et al. | 436/73 |

OTHER PUBLICATIONS

Rouilly et al, "Natural Ionophore–Based Selective Electrode for Assaying the Activity of Magnesium in Undiluted Blood Serum", *Clinical Chemistry*, vol. 36, No. 3, pp. 466–469, (1990).

Eugter et al, "Characterization Procedure for Ion–Selective Electrode Assays of Magnesium Activity in Aqueous Solutions of Physiological Composition", *Clin. Chem.*, 39/5, pp. 855–859, (1993).

*Primary Examiner*—T. Tung
*Attorney, Agent, or Firm*—Ernest V. Linek

[57] ABSTRACT

The present invention is a reagent which, when added as a conditioning solution to samples containing calcium and magnesium, selectively converts the calcium into a complex which does not interfere with magnesium ISEs, and thus allows accurate magnesium determinations by ISE in a wide variety of samples. The conditioning solution also eliminates strontium and barium interferences by the same mechanism, but these are of secondary importance because they occur in samples less frequently and because they interfere less severely. Also, the formulation of the reagent was optimized solely in order to eliminate calcium interference and its ability to remove strontium and barium interferences was surprisingly fortuitous.

17 Claims, No Drawings

INTERFERENCE SUPPRESSING BUFFER

BACKGROUND OF THE INVENTION

Several methods are available to assay for the presence or concentration of a predetermined analyte, like an ion, in a test sample. These materials include wet phase and dry phase colorimetric assays, and assays based on flame photometry, atomic absorption photometry, ion selective electrodes (ISEs) and multiple liquid phase partitioning. Recently, the ion selective electrode method of analysis has been more widely used, especially in regard to automated systems, as improvements in ion selective electrodes have developed. In particular, ion selective electrodes now have sufficient selectivity, sensitivity and operating lifetimes to be useful in automated systems. See for example, U.S. Pat. Nos. 3,598,713; 3,502,560; 3,562,129; 3,691,047; 3,753,887; 4,839,020; 4,818,361; 4,743,352; 4,713,165; 4,810,351; 5,174,872; and 5,288,388.

The use of ISEs in the analysis and monitoring of charged as well as neutral species and gases has been continuously expanding. See for example, Ruzicka J. et al., *Anal Chim. Acta*, 62, 15–28 (1972); Ruzicka J. et al., *Chr. Anal Chim. Acta*, 67, 155–78 (1973); Hulanicki A., et al., *Analust*, 107, 1356–62 (1982); Stevens C. A. et al., *Anal Chim. Acta*, 248, 315–21 (1991). Even though the symmetric ISEs have found a wide range of applications they still have certain inherent limitations. They are mechanically complicated, and thus difficult to manufacture in small size; the internal solution increases the system impedance, and finally, due to internal compartment, they cannot withstand high pressures. See for example, Selig W., *Anal Letters*, 15(A3), 309–29 (1982); Cattral R. W., et al. *Ion Selective Electrode Rev.*, Vol. 6, pp. 125–71 (1984); Nikolsky B. P. et al., *Ion Selective Electrode Rev.*, Vol. 7, pp. 3–39 (1985); Cunningham L. et al., *Analytica Chimica Acta*, 180, 271–79 (1986).

In the past 10 years, various magnesium ion-selective electrodes (ISEs) have been described in the literature. See for example, Behm F. et al., *Helv. Chim. Acta*, 68, 110–118 (1985); Rouilly M. V. et al., *Anal. Chem.*, 60, 2013–2016 (1988); Müller M. et al., *Mikrochim. Acta*, III, 283–290 (1988); Maj-Zurawska M. et al., *Anal Chim. Acta*, 218, 47–59 (1989); Maj-Zurawska M. et al., *Anal Chim. Acta*, 236, 331–335 (1990); Rouilly M. et al., *Clin. Chem.*, 36, 466–469 (1990); Hu Z. et al., *Anal Chem.*, 61, 574–576 (1989); Lewenstam A., *Anal Proc.*, 28, 106–109 (1991); Spichiger U. E. et al., *Fresenius J. Anal Chem.*, 341, 727–731 (1991); Spichiger U. E. et al., *Magnesium-Bulletin*, 13(4), 140–144 (1991); Spichiger U. E. et al., *2nd Bioelectroanalytical Symposium*, pp. 185–211 (1992); Schaller U. et al., *Pflügers Arch.*, 423, 338–342 (1993); O'Donnell J. et al., *Anal Chim. Acta*, 281, 129–134 (1993); Eugster R. et al., *Clin. Chem.*, 39, 855–859 (1993); and O'Donnell J. et al., *Mikrochim. Acta*, 113, 45–52 (1994).

A drawback to most of these electrodes is lack of satisfactory discrimination of magnesium in the presence of other divalent alkaline earth metals, notably calcium. Calcium ions are usually present in samples to be analyzed for magnesium ions, and in fact, the calcium ion concentration is often higher than the magnesium ion concentration. Thus, practical application of magnesium ISEs is often quite restricted. The present invention provides a buffer solution which eliminates the competition effects of calcium for the determination of magnesium concentrations in solution.

SUMMARY OF THE INVENTION

In the present invention, a reagent for use with magnesium ion-selective electrodes (ISEs) has been developed. Insufficient selectivity of magnesium ISEs over calcium ions has been overcome by pretreatment of test samples containing both calcium and magnesium (and/or barium and/or strontium as discussed below) with a chelating agent which selectively binds the interfering ions, i.e., calcium, barium, and/or strontium, allowing an unfettered determination of the magnesium ion concentration by the ISE.

In addition to complexing calcium ions, it has been found that the conditioning solution of the present invention also eliminates strontium and barium ion interferences by the same mechanism, i.e., by complexation. While these ions are generally considered to be of secondary importance because they occur in samples less frequently and because they interfere less severely, it is important to note that any interference thereby is eliminated by use of the conditioning solution of the present invention.

The present invention is thus directed to a reagent mixture which, when added as a conditioning solution to analytical samples suspected of containing both magnesium ions and ionic species which would interfere with the accurate determination thereof, particularly calcium ions, and selectively converts any interfering (e.g., calcium) ions into a complex which does not interfere with the determination of the magnesium ion concentration by a magnesium ISE, and thus allows accurate magnesium ion determinations by the ISE in a wide variety of samples.

Thus, in its most preferred embodiment, the formulation of the present conditioning reagent has been optimized to eliminate calcium interference and the ability of this solution to further remove strontium and barium interferences is surprisingly fortuitous. Therefore, while the following detailed description of the invention focuses on the complexation of calcium ions, the discussion applies equally to the metals strontium and barium as well.

In addition to complexing the aforementioned interfering metal ions, the reagent solution of the present invention also fixes the sample pH to fall within a specified range and advantageously counteracts the shift in pH which can occur as a result of the metal complexation reaction.

DETAILED DESCRIPTION OF THE PREFERRED EMBODIMENT

The present invention is directed to a reagent which, when added as a conditioning solution to samples containing calcium and magnesium, selectively converts the calcium into a complex which does not interfere with magnesium ISEs, and thus allows accurate magnesium determinations by ISE in a wide variety of samples.

The present inventors have discovered the existence of a narrow pH window (pH 6.5±0.5) where selective binding of calcium results in at least a 100-fold enhancement of the apparent selectivity constant for this electrode for magnesium over calcium. Use of a suitable buffered reagent containing a selective calcium binding ligand, operating in this narrow pH window, allowed the determination of magnesium in a variety of samples containing excess calcium. Some of these results are shown below in Table I, compared to atomic absorption spectroscopy (AAS) and capillary electrophoresis (CE).

TABLE I

| Sample | Mg by ISE (mg/kg) | Mg by other method (mg/kg) | Other Method |
|---|---|---|---|
| Tap H$_2$O (Boston) | 0.80 | 0.81 | CE |
| Mineral[1] H$_2$O | 8.1 | 7.8 | AAS |
| Tap H$_2$O Crete | 12.5 | 12.3 | AAS |
| Antacid[2] Tablets | 28.0 | 29.4 | CE |
| Spinach | 7050 | 6950 | AAS |

[1]Mg = 6.5 mg/kg; Ca = 101.6 mg/kg according to label.
[2]milligrams of Mg per tablet; Ca = ~165 mg according to label.

The subject reagent solution advantageously contains the following components:

(1) a complexing agent which preferentially complexes with calcium over magnesium; preferably the complexing ligand EGTA (ethylenebis(oxyethyleneitrilo) tetraacetic acid), (2) and at least one, preferably two pH buffering agents, capable of providing and maintaining a pH of about 6.5.

Although EGTA is the preferred primary complexing component, pH buffering is essential herein as well. The function of EGTA is to bind or "mask" calcium. EGTA has been shown to be an efficient complexing agent for both calcium and magnesium in other systems; see for example U.S. Pat. Nos. 4,383,043; 5,049,673 and 5,141,627. In A. Ringbom, "Complexation in Analytical Chemistry," pp. 236–7, John Wiley & Sons, New York (1963), EGTA was used to allow the separation of calcium and magnesium in an ion-exchange column. Addition of EGTA to the sample allowed the magnesium to be removed by passage through a cation-exchange column; the calcium remained in the sample as the calcium-EGTA complex, while magnesium is removed as the divalent ion, $Mg^{+2}$. In Jeffrey et al., "Vogels' Textbook of Quantitative Chemical Analysis," 5th Ed. pp. 331–2, John Wiley & Sons, New York, Eds. (1989), the concentration of calcium ions was determined in the presence of magnesium ions by titrating with EGTA. Use of the more well-known titrant, EDTA, would have yielded a result equivalent to the sum of the calcium and magnesium ion concentrations. By using the more selective titrant EGTA, the magnesium concentration was not determined and the analysis was specific only for calcium.

Thus, while the prior art was aware of, and had previously made use of EGTA's stronger complexation for calcium ions over magnesium ions, none of the previous exploitation of this chemistry had taught or suggested the exploitation thereof as taught herein. The use of EGTA, in a narrow pH range for selective complexation to minimize interference in ISE determinations of magnesium ion concentration is not an obvious extension of the prior art, for the following reasons:

(1) the narrow pH window in which the complexation of calcium but not magnesium can occur;

(2) the need for the solution to be strongly buffered at that pH so that formation of the calcium complex does not disturb the pH;

(3) the need of the pH buffering compounds themselves not to interact with magnesium or interfere with the electrode response;

(4) the requirement that the pH window must be at a pH where hydrogen ion does not interfere with the magnesium electrode; and (5) the fact that while calcium interference has long been recognized in the use of magnesium ISEs, no known prior art teaches or suggests the use of EGTA for the suppression thereof.

Thus, while EGTA is an important part of the present invention, the role of pH buffering in the present invention has several critical functions:

(1) to establish the sample pH in a narrow range (6.0–7.0) which promotes the formulation of the calcium-EGTA complex but minimizes formation of a magnesium-EGTA complex;

(2) to prevent pH (hydrogen ion) interference on the response of the magnesium electrode; and (3) to stabilize the pH, i.e., minimize the pH shift which occurs when EGTA complexes calcium (two hydrogen ions are displaced from the EGTA in forming the calcium complex).

Function (3) is very important because EGTA also complexes magnesium to a slight degree at the optimum pH for this analytical technique (optimum pH=6.5±0.1). However, this slight degree of complexation does not adversely affect the magnesium determination as long as it remains constant. However, a shift in pH will change the degree of magnesium complexation, causing an error. This effect will be illustrated in greater detail below.

In addition to the specialized function of the subject reagent to eliminate calcium ion interference, it plays the more general role of a sample conditioning (or preconditioning) reagent. Sample conditioning is routine in ISE analysis. An ISE response signal (potential) is a function of analyte ion activity. Ion activity is an arcane quantity, used chiefly in theoretical chemistry. With the exception of hydrogen ion activity (pH) measurements and some other relatively sophisticated corrosion studies and some biological applications, analysts using ISEs are interested in measuring ion concentrations, not activities. The relationship between activity and concentrations is complex when the sample matrix (e.g., pH and ionic strength) is variable. Techniques for converting activity values to concentration values are too involved and uncertain to be of use to the typical analyst performing routing concentration determinations.

Thus, the use of a conditioning reagent to eliminate the variation in solution matrices by adjusting the pH and ionic strength of all standardizing and sample solutions to the same values is an integral part of ISE methodology.

The particular magnesium electrode for which this reagent was developed is a membrane ISE described by Simon et al., as Membrane I in J. Anal Chem., 341,727–731 (1991), the disclosure of which is hereby incorporated herein by reference. This conditioning reagent will also be useful with many other types of magnesium ion-selective electrodes, particularly if enhanced selectivity for magnesium over calcium is desired, and more particularly in an application where use of a sample conditioning reagent is acceptable.

As discussed above, in addition to the complexing agent, the reagent mixture of the present invention requires at least one, and preferably at least two buffers. Buffers can be weak acids, which can be designated "HA", or weak bases which can be designated "B". The buffer of choice in this application could be either an acid or a base, providing that it's $pK_a$ value is in the range of interest, which for this discussion is designated as being between 6.0 and 7.0.

The following chemical and algebraic equations thus illustrate the relationship between $pK_a$ values, pH, and the chemical behavior of acidic and basic buffer substances:

$$pK_a \rightarrow \log K_a \qquad \text{eq 1}$$

$$HA \rightarrow H^+ + A^- \qquad \text{eq 2}$$

$$BH^+ \rightarrow B + H^+ \qquad \text{eq 3}$$

$$K_a = \frac{[H^+] + [A^-]}{(HA)} \qquad \text{eq 4}$$

$$K_a = \frac{[H^+] + (B)}{[BH^+]} \qquad \text{eq 5}$$

$$\text{pH} = pK_a \cdot \log \frac{[H^-]}{[HA^-]} \qquad \text{eq 6}$$

$$\text{pH} = pK_a \cdot \log \frac{(B)}{[HB^+]} \qquad \text{eq 7}$$

where $K_a$ in eq 4 represents the $K_a$ value for the acid HA and in eq 5 represents the value of $K_a$ for the base B, and the symbols in parentheses represent the activities in solution of the species enclosed therein.

A buffer substance is most effective when half neutralized (i.e., when pH=$pK_a$) as can be divined from an examination of eqs 6 and 7. In the case of an acid that would be when (HA) equals (A$^-$); and in the case of a base, when (B) equals (BH$^+$). In cases such as this, i.e., where buffering occurs near neutral pH, the concentration of hydrogen ion (H$^+$) is negligible. Therefore, some other ion, which normally plays no direct buffering role and thus does not appear in the above equations, must be present in order to maintain electroneutrality. This other ion is provided by the base which is used to achieve half neutralization of an acid buffer, or by the acid which is used to achieve half neutralization of a basic buffer. Thus, in the case of an acid buffer, the base which is used for half neutralization will provide a cation (positive ion) to balance the presence of the anion (negative ion) A. The importance of this cation will become clear from the following discussion.

Magnesium electrodes are sensitive primarily to the cation magnesium, but also to other cations to a greater or lesser extent, as already explained with regard to calcium. It is important, therefore, that the base used to half neutralize the acid buffer not provide a cation which interferes with the magnesium electrode. This requirement is important in understanding why it was found especially advantageous to use two buffers, i.e., both an acid buffer and a basic buffer, in the preferred conditioning reagent of the present invention.

If only one type of buffer were used, twice as high a concentration would be required to give the same buffering capacity. This would result in the presence of a cation in the buffer system, at twice the concentration that is present in the described MES/bis-tris buffer system. If only an acid buffer were used, the cation would be provided by the base which was used to half neutralize the acid; if only a basic buffer were used, the cation would be the ion BH$^+$. All cations, when present at sufficiently high concentrations can, be expected to interfere to some extent. Even the preferred mixed buffer of Example 3 degrades the measurement at low magnesium concentrations due to the presence of the bis-tris cation. Therefore, the use of a two-buffer system as described herein, is an especially preferred embodiment of this invention.

The need to maintain as low a cation concentration as possible while having as high a buffer capacity as possible imposes some additional constraints. Many acids and bases have more than one acidic and/or basic functionality, i.e., more than one $pK_a$ value, sometimes written as $pK_1$, $pK_2$, and so on, or referred to as the first, second, third, etc. $pK_a$.

If acids or bases with more than one $pK_a$ are used, it's essential that the first $pK_a$ of the acid and last or highest $pK_a$ of the base be the one with the desired value. For example, if the second $pK_a$ of the acid is used, it's first acidic functionality (first $pK_a$) will have to be completely neutralized before half neutralization of the second can occur. This results in a cation concentration at least three times as high in order to obtain the same buffer capacity. Therefore, when acids with more than one $pK_a$ (polyprotic acids) are used, it is important that it be the first $pK_a$ that has the appropriate value. When the base has more than one $pK_a$, another undesirable situation arises: at the pH value at or near the desired $pK_a$, unless the last or highest $pK_a$ is used, less buffer capacity will result, because cations from the base will have a higher charge than +1 and therefore a lower concentration will be required to half neutralize the acid. Also, cations with charges greater that +1 (polyvalent cations), especially those with a charge of +2 (divalent cations), (polyvalent cations), especially those with a charge of +2 (divalent cations), tend to interfere more with the magnesium electrode. Therefore, when polyprotic bases are used, it is necessary that the last or highest $pK_a$ be the one with the appropriate value.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLES

The three following examples help to illustrate the use of the interference suppressing buffer as a conditioning reagent in a typical ISE method. Four magnesium standard solutions were used; the concentrations were $10^{-5}$, $10^{-4}$, $10^{-3}$, and $10^{-2}$ moles/liter magnesium respectively; in each case 90 mL of the standard solutions were mixed with 10 mL of sample conditioning reagent prior to measurement.

Example 1

In Example 1, the conditioning reagent had the following composition:

0.45 moles/liter MES (4-Morpholine-ethane-sulfonic acid)

0.56 moles/liter Bis-tris (2,2-Bis(hydroxymethyl)-2,2',2''-nitrolio-triethanol)

Mixing 90 mL of standard solution with 10 mL of this conditioning reagent resulted in solutions with pH values of 6.5 and ionic strength values of 0.05 moles/liter. Unknown sample solutions with relatively low ionic strength and pH buffering capacities can be similarly conditioned with the reagent so that they will have pH and ionic strength values fixed at 6.5 and 0.05 respectively prior to measurement. This allows their magnesium concentration values to be determined by comparison of the magnesium electrode potential to the calibration curve, assuming that there are no ions in the samples which interfere. When the simulated sample, described in the previous paragraph, was analyzed using this conditioning reagent, an electrode reading corresponding to $8 \times 10^{-4}$ moles/liter magnesium was obtained. This is an analytical error of 800%, caused by the presence of calcium.

Example 2

In Example 2, the conditioning reagent has the following composition:

0.25 moles/liter MES 0.56 moles/liter Bis-Tris 0.10 moles/liter EGTA

The principal difference here is the presence of EGTA. Also, 0.02 moles per liter less of MES was necessary to establish the pH, since EGTA, like MES, is an acid and has twice the acidity per mole of MES. The pH and ionic strength of the solutions are again fixed at 6.5 and 0.05 as in the previous example. In this case, when the simulated sample was analyzed, an error still occurred, yet it was only 30%. This error was at first interpreted as failure of the EGTA to completely eliminate the calcium interference. However, it was observed that the pH of the simulated sample after treatment with the conditioning solution was 6.2 rather than 6.5. This was because each calcium ion complexed by EGTA displaced two hydrogen ions and the pH buffer capacity of the solution was insufficient to prevent such a pH shift. When the pH of this solution was re-adjusted to pH 6.5 by the addition of more bis-tris, the potential assumed a value corresponding to $10^{-4}$ moles/liter magnesium, the correct analytical result.

The explanation for this behavior lies in the slight degree of complexation of magnesium by EGTA. As explained above, this degree of complexation is not great enough to prevent accurate magnesium determination if it remains constant; however, when the pH is lowered, the degree of complexation is diminished and a small amount of magnesium is released. In this experiment, when the pH was re-adjusted, the magnesium was re-complexed. This indicated that EGTA is capable of removing the calcium interference, if the pH can be maintained at a constant value.

Example 3

In Example 3, the conditioning reagent has the following composition:

1.00 moles/liter MES 1.57 moles/liter Bis-tris 0.10 moles/liter EGTA

Here, the concentration of the pH buffering components was substantially increased, and the result was that the correct magnesium concentration was determined for the simulated sample despite the presence of excess calcium. The pH of the sample was slightly shifted due to calcium complexation, but the magnitude of the shift, −0.08 pH units, was not great enough to cause a significant error.

To summarize the three examples: in Example 1, it was demonstrated that calcium interferes strongly with this magnesium electrode; in Example 2, it was demonstrated that EGTA can eliminate the interference; and in Example 3, it was demonstrated that a large buffer capacity was required in order to eliminate the need to individually adjust each sample pH, a procedure which would be extremely cumbersome in an analytical method.

Examples 1–3 serve to emphasize the importance of the role played by pH buffering in the interference suppressing reagent. Although buffering a solution to maintain a particular pH range is routine in chemistry, selecting buffers which meet all the criteria for a particular application from among hundreds of potentially satisfactory substances can be a laborious process. The important buffer criteria in this application were:

1. $pK_a$ values (buffer points) near 6.5 (6.5±0.5)
2. high water solubility (>1.0 moles/liter)
3. not reactive to magnesium
4. not an interference for the magnesium electrode
5. readily available and/or not expensive The above limitations on choice of buffer materials became apparent while performing the following two experiments:

Exp. A  The base ethylenediamine was tried in place of bis-tris with the acid MES. Ethylenediamine has a $pK_1$ of 6.85 and a $pK_2$ of 9.93. At a pH near 6.5, the divalent ethylenediammonium ion was present and interfered with the magnesium electrode. Also, less buffer capacity was obtained because the polyprotic nature of ethylenediamine resulted in less of it being required to half neutralize the MES.

Exp. B  The diprotic acid, maleic acid, with a $pK_1$ of 1.91 and a $pK_2$ of 6.33 was tried in place of MES, using bis-tris as the base. Three times as much bis-tris was required than when MES was used, because $pK_1$ of maleic acid had to be neutralized before $pK_2$ could be half neutralized. The higher concentration of bis-tris interfered with the magnesium electrode to the extent that the lower limit of magnesium detection was increased by a factor of ten compared to when the preferred formulation with MES and bis-tris was used.

Thus, it can be postulated that other acids, whose first or only acid functionality has a $pK_a$ value between 6 and 7, and other bases whose last or only basic functionality has a $pK_a$ value between 6 and 7, may also be candidates for buffer substitution in this application. Based upon experience to date and the similarity in structure and properties compared to MES and bis-tris, the following specific acids or bases are likely to be potential substitutes for MES or bis-tris in this application (See Table II below). The skilled artisan, upon consideration of the teachings of this specification, may determine other useful combinations of buffers, without resort to any undue experimentation.

The buffers MES and bis-tris were found to meet the criteria stated above and to be a compatible acid-based pair. The solution shown in Example 3 is at this time the preferred embodiment this invention.

TABLE II

| Acid or Base | Abbreviation | $pK_a$ |
| --- | --- | --- |
| N-(2-Acetamido)iminodiacetic acid | ADA | 6.62 |
| Piperazine-N,N'-bis-(2-ethanesulfonic acid) | PIPES | 6.80 |
| 1,3-bis[tris(hydroxymethyl)-methylamino]propane | Bis-tris | 6.90 |
| N-(2-Acetamido)-2-aminoethane-sulfonic acid | ACES | 6.88 |
| 3-(N-Morpholino)-2-hydroxy-propanesulfonic acid | MOPSO | 6.75 |

OTHER CONSIDERATIONS

The choice of a pH value between 6 and 7 as set forth herein was based on two principal considerations: (1) promotion of calcium complexation and inhibition of magnesium complexation; and (2) prevention of hydrogen ion interference with the specific magnesium electrode used herein. Those having ordinary skill in this art will recognize that other magnesium electrodes may have better selectivity for magnesium ions over hydrogen ions. In such cases, it may be possible to employ a conditioning reagent based on EGTA which has a preferred pH which is slightly different than that disclosed herein. Also, a different magnesium electrode may have better selectivity over other cations such as the ethylenediammonium ion and therefore could be used with a solution containing it as buffering agent. In any case, the principles of employing a magnesium electrode conditioning reagent to minimize interference as disclosed herein would still be applicable.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A sample conditioning solution for magnesium ion-selective electrodes consisting essentially of:
   (a) ethylenebis(oxyethyleneitrilo)tetraacetic acid (EGTA), which preferentially complexes with calcium ions over magnesium ions; and
   (b) at least one pH buffering agent maintaining a stable pH in the range of about 6.0 to about 7.0.

2. The reagent solution of claim 1, wherein the stable buffered pH range is from about 6.25 to about 6.75.

3. The reagent solution of claim 1, wherein the stable buffered pH range is from about 6.4 to about 6.6.

4. The reagent solution of claim 1, which contains a second pH buffer agent, compatible with the one pH buffer agent.

5. The reagent solution of claim 4, wherein the buffer agents are 4-Morpholine ethane sulfonic acid (MES) and 2,2-Bis(hydroxymethyl)-2,2',2"-nitrolio-triethanol (Bis-tris).

6. A sample conditioning solution for magnesium ion-selective electrodes consisting essentially of:
   (a) ethylenebis(oxyethyleneitrilo)tetraacetic acid (EGTA), which preferentially complexes magnesium interfering ions selected from the group consisting of calcium, strontium, barium and mixtures thereof; and
   (b) at least one pH buffering agent maintaining a stable pH in the range of about 6.0 to about 7.0.

7. The reagent solution of claim 6, wherein the stable buffered pH range is from about 6.25 to about 6.75.

8. The reagent solution of claim 6, wherein the stable buffered pH range is from about 6.4 to about 6.6.

9. The reagent solution of claim 6, which contains a second pH buffer agent, compatible with the one pH buffer agent.

10. The reagent solution of claim 9, wherein the buffer agents are 4-Morpholine ethane sulfonic acid (MES) and 2,2-Bis(hydroxymethyl)-2,2',2"-nitrolio-triethanol (Bis-tris).

11. A sample conditioning solution for magnesium ion-selective electrodes consisting essentially of:
    (a) ethylenebis(oxyethyleneitrilo)tetraacetic acid (EGTA), which preferentially complexes magnesium interfering ions selected from the group consisting of calcium, strontium, barium and mixtures thereof; and
    (b) a mixture of at least two buffering agents maintaining a stable pH of about 6.5.

12. The reagent solution of claim 11, wherein one of the buffering agents is 4-Morpholine ethane sulfonic acid (MES).

13. The reagent solution of claim 11, wherein one of the buffering agents is 2,2-Bis(hydroxymethyl)-2,2',2"-nitrolio-triethanol (Bis-tris).

14. A method of minimizing calcium ion interference when measuring the magnesium ion concentration in a sample solution with a magnesium ion selective electrode, said method comprising treating a sample solution including calcium and magnesium ions with a sample conditioning solution consisting essentially of:
    (a) ethylenebis(oxyethyleneitrilo)tetraacetic acid (EGTA), which acts as a complexing agent; and
    (b) a mixture of at least two buffering agents maintaining a stable pH of about 6.5.

15. The method of claim 14, wherein said treating step also minimizes interference from barium ions present in the sample solution.

16. The method of claim 14, wherein said treating step also minimizes interference from strontium ions presnet in the sample solution.

17. The method of claim 14, wherein the buffer agents are 4-morpholine ethane sulfonic acid (MES) and 2,2-Bis (hydroxymethyl)-2,2',2"-nitrolio-triethanol (Bis-tris).

* * * * *